(12) United States Patent
Donzier et al.

(10) Patent No.: US 10,761,238 B2
(45) Date of Patent: *Sep. 1, 2020

(54) DOWNHOLE OPTICAL CHEMICAL COMPOUND MONITORING DEVICE, BOTTOM HOLE ASSEMBLY AND MEASUREMENTS-WHILE-DRILLING TOOL COMPRISING THE SAME, AND METHOD OF OPTICALLY MONITORING CHEMICAL COMPOUND DOWNHOLE DURING DRILLING

(71) Applicant: Openfield SA, Versailles (FR)

(72) Inventors: Eric Donzier, Berchères sur Vesgre (FR); Linda Abbassi, Montigny le Bretonneux (FR); Emmanuel Tavernier, Paris (FR)

(73) Assignee: OPENFIELD SA, Versailles (FR)

( * ) Notice: Subject to any disclaimer, the term of this patent is extended or adjusted under 35 U.S.C. 154(b) by 207 days.

This patent is subject to a terminal disclaimer.

(21) Appl. No.: 15/806,892

(22) Filed: Nov. 8, 2017

(65) Prior Publication Data

US 2018/0128937 A1    May 10, 2018

(30) Foreign Application Priority Data

Nov. 8, 2016   (EP) ..................... 16306471

(51) Int. Cl.
*G01V 8/12*    (2006.01)
*G01N 21/85*   (2006.01)
(Continued)

(52) U.S. Cl.
CPC ............... *G01V 8/12* (2013.01); *E21B 47/01* (2013.01); *E21B 47/113* (2020.05); *E21B 49/08* (2013.01);
(Continued)

(58) Field of Classification Search
CPC ...... G01V 8/12; G01N 21/8507; G01N 21/27; G01N 33/2823; G01N 21/25; G01N 21/31;
(Continued)

(56) References Cited

U.S. PATENT DOCUMENTS

| 4,492,865 A | 1/1985 | Murphy |
| 5,237,857 A | 8/1993 | Dobson |

(Continued)

FOREIGN PATENT DOCUMENTS

| EP | 2292895 A2 * | 3/2011 | ........... G01N 33/287 |
| EP | 3091174 A1 | 11/2016 | |

OTHER PUBLICATIONS

EP16306471, European Search Report, dated Apr. 12, 2017, Munich, Germany.

*Primary Examiner* — Dominic J Bologna
(74) *Attorney, Agent, or Firm* — The Jansson Firm; Pehr B. Jansson (57) ABSTRACT

A downhole optical chemical compound monitoring device (30) arranged to be integrated in a mandrel (20) of a drilling system, for monitoring a chemical compound in a drilling fluid (14B) circulated through a well (7, 8), the downhole optical chemical compound monitoring device (30) comprising:
 an analysis cell part (31) comprising an open cavity (40, 140) into which the drilling fluid (14B) is free to flow;
 a first optical probe (41A, 141A) coupled to a light source (157) and arranged to transmit a light energy into the open cavity (40, 140);
 a second optical probe (41B, 141B) coupled to a detector (158) and arranged to produce in use a signal resulting from an interaction of the drilling fluid (14B) present in the open cavity (40, 140) with said light energy, indicative of a quantity of chemical compound present in the drilling fluid (14B);

(Continued)

each of said optical probes is mounted through a wall (38A, 38B, 138A, 138B) of the analysis cell part (31) in a sealed manner and has a tip (45A, 45B), the tip being needle shaped and having an external diameter less than 1 mm; and the first optical probe (41A, 141A) and the second optical probe (41B, 141B) are arranged such that the first and second tips of the respective optical probes project into the open cavity (40, 140) and such that the first tip (45A) of the first optical probe (41A, 141A) faces the second tip (45B) of the second optical probe (41B, 141B) at a defined distance ranging from 10 μm to 10 mm.

19 Claims, 9 Drawing Sheets

(51) Int. Cl.
| | |
|---|---|
| *E21B 47/01* | (2012.01) |
| *E21B 47/113* | (2012.01) |
| *E21B 49/08* | (2006.01) |
| *G01N 21/27* | (2006.01) |
| *G01N 33/28* | (2006.01) |

(52) U.S. Cl.
CPC ......... *G01N 21/27* (2013.01); *G01N 21/8507* (2013.01); *G01N 33/2823* (2013.01); *E21B 49/0875* (2020.05)

(58) Field of Classification Search
CPC ........ E21B 47/01; E21B 47/102; E21B 49/08; E21B 2049/085
See application file for complete search history.

(56) References Cited

U.S. PATENT DOCUMENTS

| | | | | |
|---|---|---|---|---|
| 6,508,105 | B1 * | 1/2003 | Vigneaux | G01N 33/2823 73/53.05 |
| 9,651,710 | B2 * | 5/2017 | Donzier | G01N 21/8507 |
| 2004/0216872 | A1 * | 11/2004 | Foster | E21B 47/01 166/250.01 |
| 2012/0175510 | A1 * | 7/2012 | Zhou | G01N 33/2823 250/255 |
| 2015/0024522 | A1 * | 1/2015 | Wang | C09D 183/04 438/26 |
| 2016/0084067 | A1 | 3/2016 | Harris | |
| 2017/0260845 | A1 * | 9/2017 | Rashid | E21B 47/011 |

\* cited by examiner

DOWNHOLE OPTICAL CHEMICAL COMPOUND MONITORING DEVICE, BOTTOM HOLE ASSEMBLY AND MEASUREMENTS-WHILE-DRILLING TOOL COMPRISING THE SAME, AND METHOD OF OPTICALLY MONITORING CHEMICAL COMPOUND DOWNHOLE DURING DRILLING

TECHNICAL FIELD

The invention relates to a downhole optical chemical compound monitoring device, a bottom hole assembly comprising such a downhole optical chemical compound monitoring device, and a measurements-while-drilling or logging-while-drilling tool comprising such a downhole optical chemical compound monitoring device. The invention is particularly applicable to the early detection of chemical compound (e.g. methane, carbon dioxide, hydrogen sulfide) during drilling operations of a hydrocarbon well in an earth formation comprising hydrocarbon bearing zones. The downhole chemical compound monitoring device, bottom hole assembly and measurements-while-drilling tool operate at downhole pressure and temperature conditions.

BACKGROUND

The document U.S. Pat. No. 6,176,323 describes a drilling system for drilling oilfield boreholes or wellbores utilizing a drill string having a drilling assembly conveyed downhole by a tubing (usually a drill pipe or coiled tubing). The drilling assembly includes a bottom hole assembly (BHA) and a drill bit. The bottom hole assembly preferably contains commonly used measurement-while-drilling sensors. The drill string also contains a variety of sensors for determining downhole various properties of the drilling fluid. Sensors are provided to determine density, viscosity, flow rate, clarity, compressibility, pressure and temperature of the drilling fluid at one or more downhole locations. Chemical detection sensors for detecting the presence of chemical species such as methane ($CH_4$), carbon dioxide ($CO_2$), hydrogen sulfide ($H_2S$), etc. are disposed in the drilling assembly. Sensors for determining fluid density, viscosity, pH, solid content, fluid clarity, fluid compressibility, and a spectroscopy sensor are also disposed in the bottom hole assembly. Data from such sensors is processed downhole and/or at the surface. Corrective actions are taken based upon the downhole measurements at the surface which may require altering the drilling fluid composition, altering the drilling fluid pump rate or shutting down the operation to clean wellbore. The drilling system contains one or more models, which may be stored in memory downhole or at the surface. These models are utilized by the downhole processor and the surface computer to determine desired fluid parameters for continued drilling. The drilling system is dynamic, in that the downhole fluid sensor data is utilized to update models and algorithms during drilling of the wellbore and the updated models are then utilized for continued drilling operations.

Such bottom hole assembly performs optical measurements using optical window.

The bottom hole assembly operates in harsh environment, namely extreme conditions including high pressure from several hundred bars up to 2000 bars, high temperature up to 200° C., presence of corrosive fluids such as sulfuric acid, presence and contamination by solid particles such as scales, asphalthenes, sand particles, as well as multiphasic flow conditions (oil, gas, water), and mud. Further, there are also is the space and power constraints associated to bottom hole assembly deployment. Furthermore, there is the high shocks environment associated to drilling operations.

The drawbacks of the design described in document U.S. Pat. No. 6,176,323 are the following:

Low performance of compositional analysis—The optical path length selection (light travel distance inside the fluid) is constrained by the fluid flow restriction that can be accepted without altering the sampling process and/or the representativeness of the fluid sample present in between the two windows. Distance between windows below 1 mm is in practice very difficult to implement and typical optical path lengths for current commercial tools are within the 2-5 mm range. This limitation has forced engineers to favor optical analysis in the visible—near infrared spectrum (i.e. 400 to 1500 nm wavelengths) where attenuation factors in hydrocarbon fluids are relatively low, despite the fact that absorption peaks are related to overtones of the vibration modes of the molecules to be detected and suffer from peak enlargements and overlaps from different compounds. This leads to complex interpretation and relatively poor robustness and performance of such compositional analysis.

Optical cell contamination—Relatively large optical window surface (several $mm^2$) and even more importantly its flat surface (large curvature ratio superior to 1 mm) favor the formation of droplets of fluids sticking on the window surface and altering analysis.

Complex and expensive hardware—The state of the art window assembly relies on sapphire disk or tube brazed onto the metal housing of the measurement cell) which critical in order to withstand high pressure and high temperature.

Optical path—The optical path length is fixed and can only be changed at the manufacturing step of the cell requiring a complete redesign of the measurement cell.

Cleaning—The complex mechanical configuration of the cell flow line and windows leads to dead volumes which make the cleaning of the cell flow line during the early phase of the sampling a critical step. In practice measurements are affected by fluid contamination and very slow to react.

SUMMARY OF THE DISCLOSURE

It may be desirable to propose a downhole optical chemical compound monitoring device that overcome one or more of the limitations of the known methods and/or devices.

According to one aspect, there is provided a downhole optical chemical compound monitoring device arranged to be integrated in a mandrel of a drilling system, for monitoring a chemical compound in a drilling fluid circulated through a well, the downhole optical chemical compound monitoring device comprising:

an analysis cell part comprising an open cavity into which the drilling fluid is free to flow;

a first optical probe coupled to a light source and arranged to transmit a light energy into the open cavity;

a second optical probe coupled to a detector and arranged to produce in use a signal resulting from an interaction of the drilling fluid present in the open cavity with said light energy, indicative of a quantity of chemical compound present in the drilling fluid;

each of said optical probes is mounted through a wall of the analysis cell part in a sealed manner and has a tip, the tip being needle shaped and having an external diameter less than 1 mm; and the first optical probe and the second optical probe are arranged such that the first and second tips of the respective optical probes project into the open cavity and such that the first tip of the first optical probe faces the second tip of the second optical probe at a defined distance ranging from 10 µm to 10 mm.

The analysis cell part may comprise a first and a second hole facing each other, a portion of the first and second optical probe being inserted into the open cavity through the first and second hole respectively, and wherein at least one optical probe is coupled in sealed manner to one of the holes, said seal and hole being adapted to enable the position of said optical probe relatively to the wall of the analysis cell part to be adjusted so as to control the defined distance between both tips.

The optical probes may be parallel to a longitudinal axis YY' of the analysis cell part.

The optical probe may comprise an optical element in the form of an optical fiber and a tip of sapphire or equivalent material located in a central portion of an elongated body in the form of a protective tube, an end portion of said optical element forming a tip end adapted to be in contact in use with the drilling fluid present in the open cavity.

The optical probe may comprise an optical element in the form of a tip of sapphire or equivalent material located in the central portion of a supporting body forming a protective housing, an end portion of said optical element forming a tip end adapted to be in contact in use with the drilling fluid present in the open cavity.

The optical probe may comprise an electronic board coupled to the optical element and integrating a measurement circuit and a processing module so as to deliver digital measurements on an output cable.

The open cavity may have a trench shape comprising an elongated part oriented substantially parallel to the longitudinal axis YY'.

The open cavity may have a trench shape comprising an elongated part oriented substantially perpendicular to the longitudinal axis YY'.

The downhole optical chemical compound monitoring device may comprise a first part and a second part respectively extending longitudinally according to the longitudinal axis YY' on each side of the analysis cell part, each part forming a protective housing, the first part comprising an optical emission electronic circuit including the light source and the second part comprising an optical reception electronic circuit including the detector.

The downhole optical chemical compound monitoring device may comprise at least one supporting part arranged to secure in a removable manner the first part and/or the second part into a corresponding recess of the mandrel of the drilling system.

The light source, respectively the detector, may transmit, respectively detect, light energy selected from ultraviolet light, visible light, or near infra-red light.

The detector is tuned to detect characteristic light energy of methane (CH4), carbon dioxide (CO2) or hydrogen sulfide (H2S).

The open cavity may have internal dimensions ranging between 2 to 15 mm.

The open cavity may be fitted with an anti-contamination filter including a buffer fluid filling the open cavity. The buffer fluid may include perfluoropolyether oil. The anti-contamination filter may further include a grid above the open cavity.

According to a further aspect, there is provided a bottom hole assembly of a drilling system comprising a mandrel having a recess positioned on a mandrel circumference, the recess being arranged to receive a downhole optical chemical compound monitoring device of the invention.

According to still a further aspect, there is provided a measurements-while-drilling or logging-while-drilling tool of a drilling system comprising a recess positioned on an external surface, the recess being arranged to integrate a downhole optical chemical compound monitoring device of the invention.

According to still a further aspect, there is provided a method of optically monitoring chemical compound downhole during drilling operations, said chemical compound being possibly present in a drilling fluid circulated through a well drilled in an earth formation comprising hydrocarbon bearing zones, said chemical compound corresponding to a risk of gas kick and/or a risk of acid corrosion, the method comprising:

close to a drilling zone, letting freely flow the drilling fluid in an open cavity of an analysis cell part, said open cavity comprising a first optical probe coupled to a light source and facing a second optical probe coupled to a detector;

illuminating the drilling fluid by means of the first optical probe with a light energy in a wavelength range wherein absorption of at least one specific radiation wavelength by said chemical compound occurs;

detecting a signal resulting from an interaction of the drilling fluid present in the open cavity with said light energy by means of the second optical probe, and analyzing a spectrum based on said transmitted electromagnetic radiations by means of a spectrometer coupled to said light detector; and estimating a risk of gas kick and/or a risk of acid corrosion during drilling operations based on a detection of a peak in said spectrum corresponding to at least one chemical compound.

The downhole chemical compound monitoring device and method of the invention is used for real time optical monitoring of chemical compounds and in particular methane ($CH_4$), carbon dioxide ($CO_2$) and/or hydrogen sulfide ($H_2S$) presence close to the drill bit of a drilling system. Thus, with the invention, it is possible to achieve an early detection of risk of methane gas kick and/or risk of acid ($CO_2$ and $H_2S$ are highly corrosive at downhole conditions) corrosion during drilling operations of a hydrocarbon well in an earth formation comprising hydrocarbon bearing zones. Further, the invention is well suited to be used in the frame of lateral wells drilling operations in gas formations.

Other advantages will become apparent from the hereinafter description of embodiments of the invention.

BRIEF DESCRIPTION OF THE DRAWINGS

The present invention is illustrated by way of examples and not limited to the accompanying drawings, in which like references indicate similar elements.

DETAILED DESCRIPTION

The invention will be understood from the following description, in which reference is made to the accompanying drawings.

Figure 1:
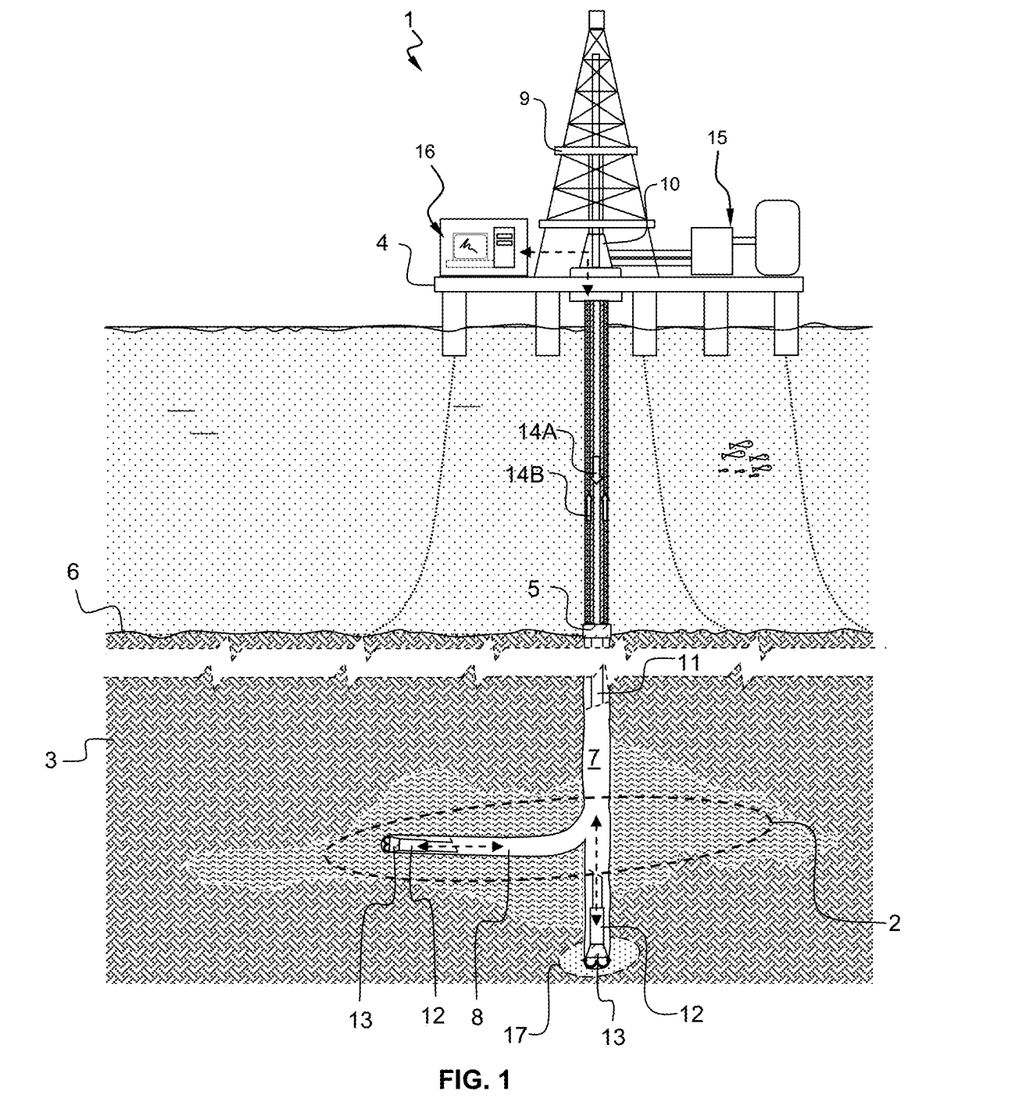
FIG. 1 schematically illustrates an offshore and subsea hydrocarbon well location and an installation for drilling an oilfield reservoir.

In the oilfield domain of application, as illustrated in FIG. 1, offshore and subsea oil equipments 1 are positioned above a zone 2 of a geological formation 3 which may be a hydrocarbon-bearing zone. The offshore and subsea oil equipments 1 may comprise a floating vessel or semisubmersible platform 4 located at the surface and a subsea well equipment 5 located on a seabed level 6. FIG. 1 depicts a well at a stage during drilling operations of the well in the earth formation 3. The well bore is shown as comprising substantially vertical portion 7 and substantially horizontal portion 8. However, it may also comprise deviated or inclined portion (not shown) having an angle from 0 to 90° relatively to a vertical axis.

A derrick 9 is erected on the platform 4 which supports a rotary table 10 that is rotated by a motor at a controlled speed. Draw-works, swivel, kelly, rotary table, blowout preventer, power unit, etc are not germane to the present invention, are well known in the art of drilling operations and are, therefore, not depicted and described in details herein. A drill string comprises a drill pipe 11 extending downward is from the rotary table 10 into the vertical portion 7 or the horizontal portion 8 of the well bore. A bottom hole assembly 12 carrying a drill bit 13 is suspended at the lower end of a string of drill pipe 11 which is supported from the surface of the earth by the surface equipment 1. A drilling fluid 14 (mud) is forced down (arrow 14A) from a drilling fluid unit 15 through the drill string through the drill bit and back up (arrow 14B) to the surface through the annulus between the drill pipe and the walls of the borehole. The drilling fluid unit 15 comprises known drilling fluid pump, injecting and returning tubings, desurger, joint, shaker/filter, mud container and clean drilling fluid container, etc that are not depicted and described in details herein. The drilling fluid 14 cools the bit 13 and carries cuttings out of the well. Further, the drilling fluid 14 imposes a hydrostatic pressure upon high-pressure formations penetrated by the drill bit in order to prevent the collapse of the bore hole and the uncontrolled flow of oil, gas or water during drilling operations. The penetration of the drill bit through subterranean formations is increased by applying a force of the drill bit against the end of the well portion (i.e. weight on the bit).

Figure 2:
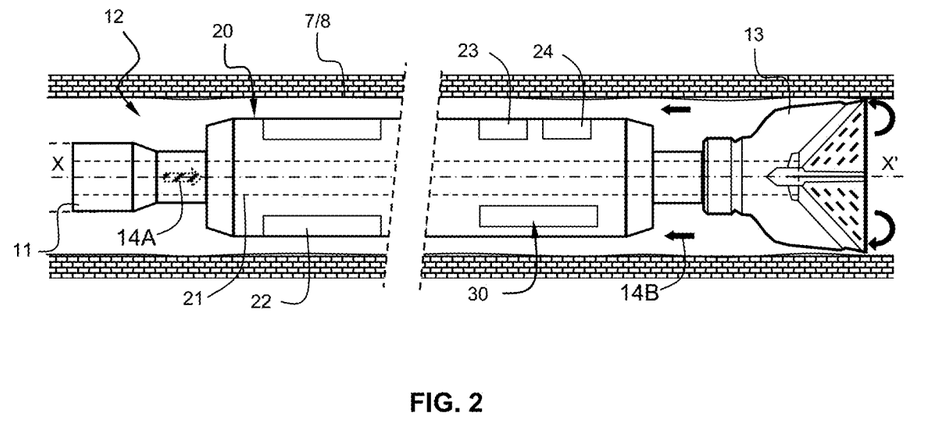
FIG. 2 is a side view schematically illustrating a part of a drilling assembly comprising a bottom hole assembly fitted with a downhole optical chemical compound monitoring device according to anyone of the embodiments of the invention.

FIG. 2 is a side view schematically illustrating a bottom hole assembly 12 supported from and connected to a tubular drill pipe 11 of the drill string through drill tool joint at one end, and connected to a drill bit 13 at the other end. The bottom hole assembly 12 is a mandrel 20, namely a hollow cylindrical member having a longitudinal axis XX' extending substantially parallel to the well bore 7 or 8. A central passage 21 extends from the drill pipe 11 towards the drill bit 13 in order to let flow the drilling fluid that is forced down towards the drill bit 13. The bottom hole assembly 12 provides force for the bit to break the rock, survive a hostile mechanical environment and provide the driller with directional control of the well bore being drilled. For these purposes, the bottom hole assembly 12 may comprise various components, e.g. anchor and thrust/pushdown equipment 22, directional drilling and measuring equipment 23, measurements-while-drilling tools/logging-while-drilling tools 24 and eventually other specialized devices. In particular, the bottom hole assembly 12 is fitted with a downhole optical chemical compound monitoring device 30 of the invention.

A processing arrangement 16 is coupled to the bottom hole assembly 12 (see FIG. 1). Further, it may also be coupled to other sensors at the surface or subsea or downhole (not shown). Furthermore, it may also be coupled to active completion devices like valves (not shown). The processing arrangement 16 may be positioned at the floating vessel or semisubmersible platform 4 located at the surface, or, alternatively, in the subsea well equipment 5 at the seabed level 6. The processing arrangement 16 may comprise a computer. It may be managed by an operator located on the floating vessel or semisubmersible platform 4. It may also be managed at a distance when the floating vessel or semisubmersible platform 4 is provided with a communication means, e.g. a satellite link (not shown) to transmit data to and receive instructions from an operator's office. The processing arrangement 16 may gather various measurements provided by various sensors related to the hydrocarbon-bearing and producing zone 2.

Downhole, a particular zone comprising methane molecules (under gas or liquid form) 17 can be encountered during the drilling operations. The bottom hole assembly 12 comprising an embodiment of a downhole chemical compound monitoring device according to the invention that will be described in details hereinafter is used for real time optical monitoring of methane presence close to the drill bit of a drilling system. When methane molecules are detected during drilling operations by the downhole chemical compound monitoring device, the operator at the surface is informed and appropriate action are taken.

Figure 3:
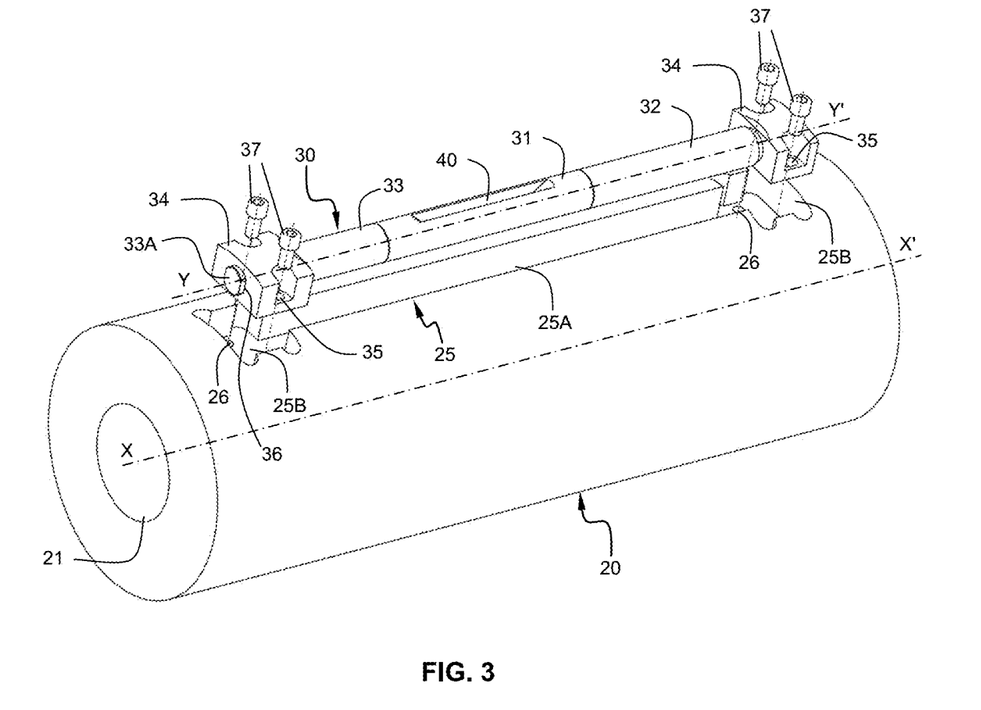
FIG. 3 is perspective partially exploded view showing a connection of a downhole optical chemical compound monitoring device according to a first embodiment of the invention to a mandrel of a bottom hole assembly.
Figure 4:
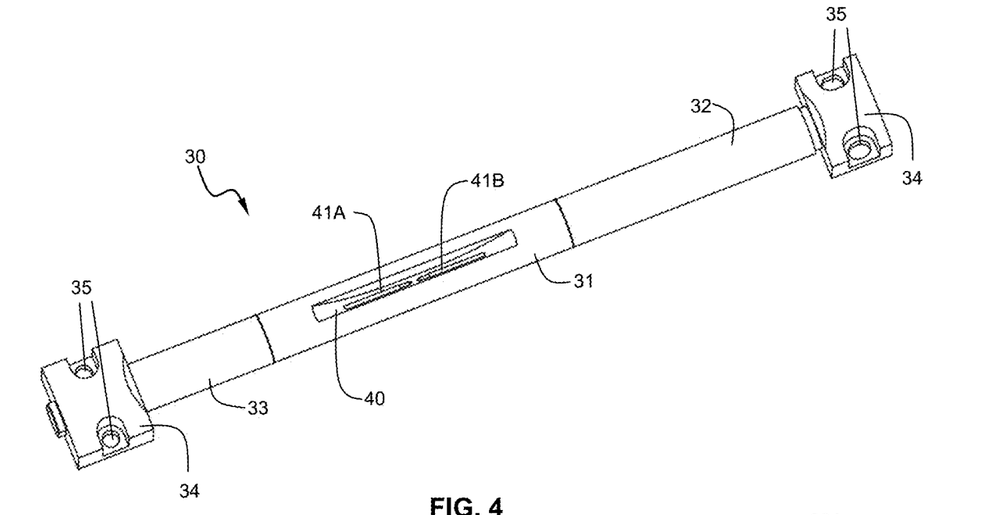
FIGS. 4, 5, 6, 7, 8 and 9 are a top perspective view, a bottom perspective view, a side view, a top view, AA and BB cross section view of the embodiment of FIG. 3, respectively.
Figure 5:
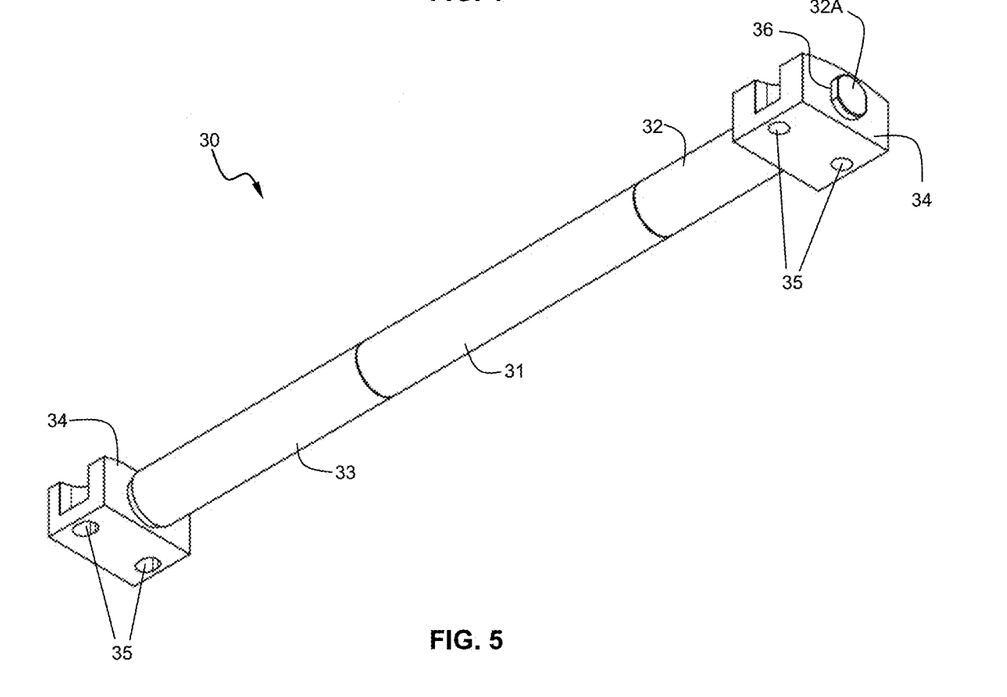
Figure 6:
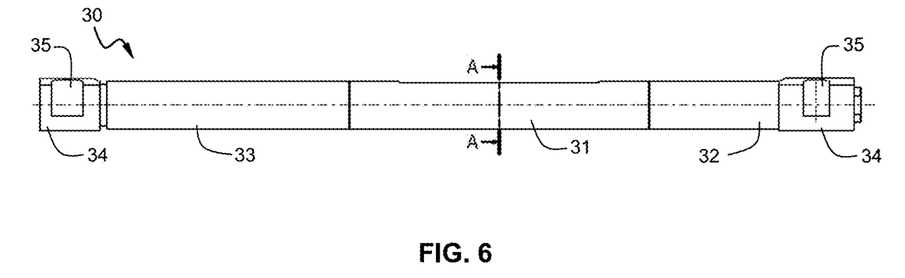
Figure 7:
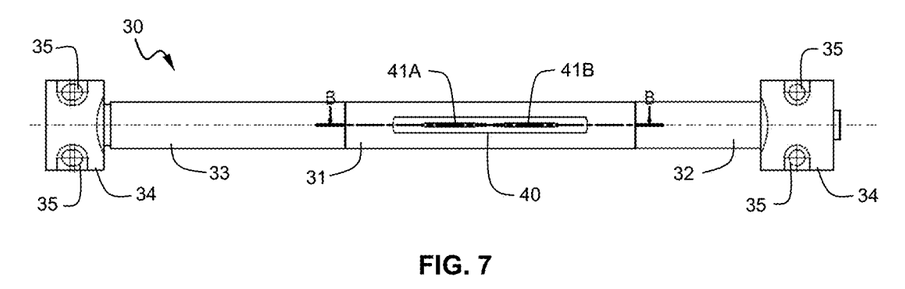
Figure 8:
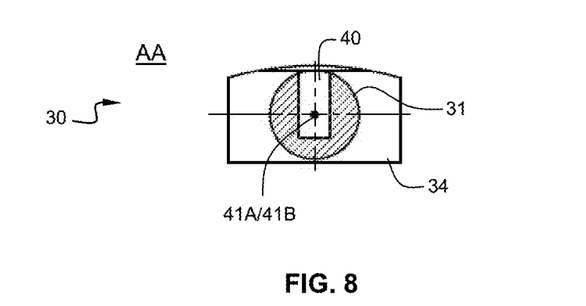
Figure 9:
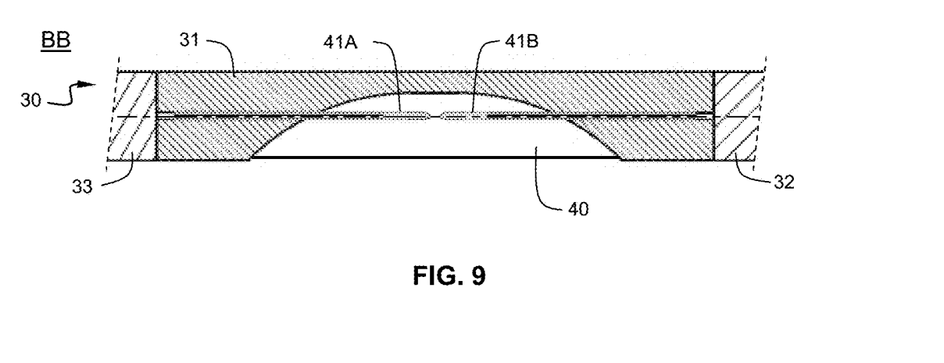

FIG. 3 is perspective exploded view showing an embodiment of the downhole optical chemical compound monitoring device 30 arranged into a mandrel 20 of a bottom hole assembly 12. FIGS. 4, 5, 6, 7, 8 and 9 are a top perspective view, a bottom perspective view, a side view, a top view, AA and BB cross section view of such embodiment, respectively.

The mandrel 20 of the bottom hole assembly 12 is a hollow cylindrical member having a longitudinal axis XX' comprising a central passage 21 to let flow the drilling fluid. The mandrel 20 comprises a recess 25 for receiving the downhole optical chemical compound monitoring device 30 such that it is fully integrated into the bottom hole assembly 12 close and behind the drill bit 13. The recess 25 extends in the external surface at the circumference of the mandrel 20 substantially parallel to the longitudinal axis XX'. The recess 25 may comprise a central elongated portion 25A extending substantially parallel to the longitudinal axis XX' and terminating, at each end, by a T-shaped portion 25B extending substantially perpendicular to the longitudinal axis XX'. The recess, for example T-shaped portion 25B, comprises multiple threaded holes 26 (only two are visible) positioned at the bottom of the recess. On the one hand, the depth of the recess 25 is such that the upper side of the downhole optical chemical compound monitoring device 30 is substantially flush with the external surface of the mandrel 20. On the other hand, the depth of the recess 25 and of the threaded holes 26 into the mandrel 20 is such that the water tightness and integrity of the mandrel with respect to pressurized fluid flowing into the passage 21 is maintained.

The embodiment of FIG. 3 comprises an optical analysis cell part 31, a first part 32 comprising the optical emission electronic, a second part 33 comprising the optical reception electronic, and two supporting parts 34.

The optical analysis cell part 31, the first part 32 and the second part 33 have a cylindrical shape extending longitudinally according to the longitudinal axis YY'. When the downhole optical chemical compound monitoring device 30 is positioned within the recess 25 of the mandrel 20, the longitudinal axis YY' of the downhole optical chemical compound monitoring device 30 is parallel to the longitudinal axis XX' of the mandrel 20. The first part 32 and the second part 33 are connected at one end to the optical analysis cell part 31, and terminate, at the other end, by a portion having at least one flat contact surface 32A and 33A for blocking in rotation the assembly comprising the optical analysis cell part 31, the first part 32 and the second part 33 into corresponding holes 36 of the supporting parts 34. Each supporting part 34 has a substantially parallelepiped shape extending substantially perpendicular to the longitudinal axis YY'. Each supporting part 34 comprises holes 35 corresponding to the threaded holes 26 of the mandrel 20. Appropriate screw 37 are inserted into said hole 35 of the supporting part 34 and screw down into the threaded holes 26 of the mandrel 20 in order to secure the downhole optical chemical compound monitoring device 30 into the recess 25 of the mandrel 20.

The optical analysis cell part 31 is a full/plain cylinder comprising an open cavity 40 extending along the longitudinal axis YY'. Further, it comprises two facing holes 39A and 39B (see FIG. 11) oriented along the longitudinal axis YY' and emerging from the facing walls 38A, 38B into the open cavity. Said holes 39A and 39B are arranged to receive two facing optical probes 41A and 41B, respectively. The open cavity 40 has a trench like shape. For example, the open cavity is rectangular in the AA cross-section (see FIG. 8) and a portion of circular sector in the BB cross-section (see FIG. 9). The open cavity 40 forms an analysis cell open towards the well bore wall where the drilling fluid 14B flowing from the drill bit 13 around the bottom hole assembly 12 towards the surface can freely flow. The open cavity may have internal dimensions (length, width, height) ranging between 2 to 15 mm.

The first part 32, the second part 33 respectively, is a hollow cylinder forming a protective housing (see FIG. 10) for receiving the electronic board 50 associated to the optical probe 41A, 41B respectively. The electronic board 50 associated to the optical probes 41A and 41B is positioned within the protective housings of the first part 32 and of the second part 33. More precisely, the first part 32 comprises the optical emission electronic circuit 57 (a controlled light source, incandescent lamp, hot plate emitter, or narrow wavelength tunable source, etc) and the second part 33 comprises the optical reception electronic circuit 58 (a spectrometer or a detector associated to filters at specific wavelengths).

Figure 10:
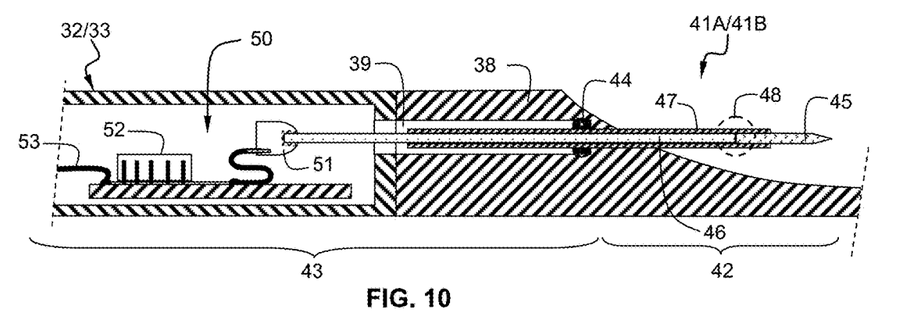
FIG. 10 is a longitudinal partial cross section view in a downhole optical chemical compound monitoring device according to the embodiment of FIG. 3.

FIG. 10 is a longitudinal cross section view in an optical probe 41A or 41B used in a downhole optical chemical compound monitoring device 30 according to the above-mentioned embodiment of the invention.

Figure 11:
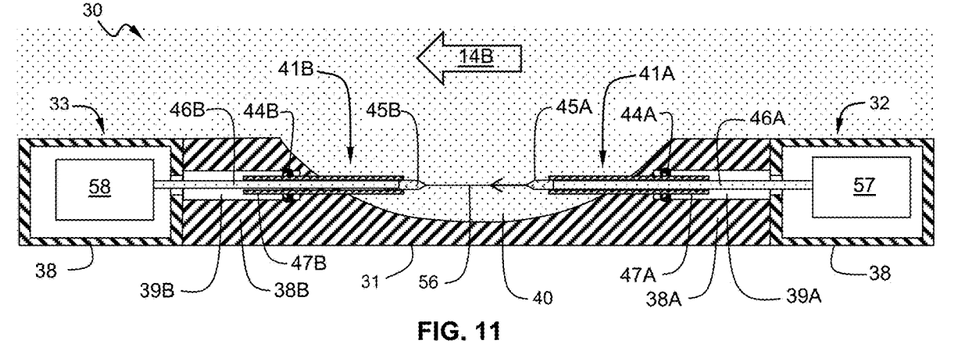
FIG. 11 is side cross section view in the embodiment of FIG. 2 illustrating the optical measurement principle.

The optical probe 41A or 41B has the general shape of an elongated cylindrical body having a first portion 42 in contact with the well fluid to be analyzed (i.e. in contact with harsh environments), and a second portion 43 separated from the fluid to be analyzed (protected from harsh environments). An appropriate seal (e.g. O-Ring) 44 separates the first portion 42 from the second portion 43. The first portion 42 comprises an optical tip 45 coupled to at least one optical fiber 46 (e.g. silica or chalcogenide glass fiber), a protective tube 47 surrounding the optical fiber 46, a coupling zone 48 between the optical tip 45 and the optical fiber 46. The protective tube 47 partially surrounds the optical tip 45 at the coupling zone 48, letting the distal part of the optical tip 45 in contact with the fluid to be measured. The second portion 43 comprises the electronic board 50 coupled to the optical fiber 46, and the protective housing of the first part 32 or the second part 33. FIG. 11 shows an embodiment comprising two optical probes 41A and 41B. The electronic board 50 may integrate an optoelectronics module comprising a measurement circuit 51 and a processing module 52 achieving light amplitude and/or spectral analysis so as to deliver digital measurements on output cables 53.

The optical tip 45 is a rod having a needle shape. A suitable material for the rod is sapphire but other materials of comparable properties can be contemplated. For the sake of convenience the term "sapphire" will be used in the following but this is not meant to exclude the use of another suitable material. The external diameter of the sapphire rod ranges from about 0.3 mm to about 1 mm. The sapphire material has a particular robustness in corrosive environments. The needle shape has the property of self cleaning in multiphasic conditions. Droplets of fluids can hardly stick on such a tip.

The protective tube 47 is made of metal or alloy. Metal or alloy offering high strength and high chemical resistance such as austenite nickel-chromium-based superalloys (e.g. known as Inconel, a registered trademark of SMC) can suitably be used. The protective tube 47 is used to mechanically maintain the sapphire rod optical tip 45 ensuring a pressure tight connection to the optical fiber 46, to protect the optical fiber 46 from fluids and to hold the seal 44. The protective tube 47 is sealed against the optical tip 45 in order to avoid penetration of fluid towards the optical fiber 46 and the second portion 43. As a particular example, the protective tube 47 has an external diameter of 0.5 mm to 3 mm, and is a few centimeters long (e.g. 25.4 cm/10 inches).

The seal 44 may slide onto the protective tube 47. This assembly is adapted to be connected into a corresponding hole 39 through the optical analysis cell part 31 and the protective housing of the first part 32 and the second part 33 as depicted in FIG. 11. This assembly enables adjusting the position of the optical probe relatively to the hole of the optical analysis cell part 31 so as to control the distance between the tips 45A and 45B of two vis-à-vis probes. The seal 44 may be made of a synthetic rubber/fluoropolymer elastomer (e.g. Viton fluoroelastomers, a registered trademark of DuPont Performance Elastomers L.L.C). A high pressure seal connection is obtained when the seal 44 associated with the protective tube 47 is appropriately inserted into the hole 39. This is only an example, as other waterproof and high pressure connections may be appropriate. As a further alternative, the connection may be a welded connection, meaning that once the distance has been set at manufacturing step, the protective tube 47 is welded to a hole in the optical analysis cell part 31. In order to avoid that the external pressure pushes back on the optical probes and to ensure that the optical probes are maintained in their respective specific positions, a mechanical bearing device (not shown) maintains each protective tube 47 into the corresponding hole 39.

FIG. 11 is side cross section view in a downhole optical chemical compound monitoring device 30 according to the above-mentioned embodiment illustrating the optical measurement principle.

The optical tips 45A, 45B respectively face each other inside the optical analysis cell part 31 where the fluid 14B is free to flow. As an example, the first tip 45A of the first probe 41A faces the second tip 45B of the second probe 41B at a defined distance ranging from 10 μm to 10 mm. One of the optical probe, for example the first optical probe 41A is used as light emitting probe by being connected to the optical emission electronic circuit 57 (e.g. controlled light source). The other optical probe, for example the second optical probe 41B is used as a light receiving probe by being connected to the optical reception electronic circuit 58 (e.g. spectrometer). An optical transmission path 56 is created between both optical tips 45A, 45B. Mid-infrared spectroscopy principle is based on absorption of specific infrared radiation wavelength from molecules. Absorption intensity varies with concentration of molecules in the drilling fluid. Those wavelengths correspond to vibration modes of the molecules. Analysis of the infrared spectrum therefore allows to measure type and concentration of chemical compounds in a sample. The absorption wavelengths of chemical compounds of particular interest are 3.33 μm for methane ($CH_4$), 4.27 μm for carbon dioxide ($CO_2$), 1.58 μm for hydrogen sulfide ($H_2S$). The optical reception electronic circuit comprising a spectrometer 58 detects a methane peak and then estimates a methane concentration into the fluid using appropriate models and calibrations data. As an alternative, the optical reception electronic circuit comprises a detector associated to a filter at specific wavelength corresponding to the specific chemical compound intended to be detected. When the methane concentration is above a defined threshold value, a warning signal can be transmitted to the processing arrangement 16.

It is possible as mentioned above to adjust the position of the first optical probe 41A, or of the second optical probes 41B, or of both probes 41A, 41B respectively relatively to the holes 39A, 39B respectively so as to control the length of the optical path 56 between both tips. This length adjustment is easy to perform by sliding probes inside the open cavity 40.

The downhole optical chemical compound monitoring device 30 provides minimal intrusion into the annulus of the well bore and minimal perturbation effect onto the fluid flow. Also, the mechanical position of both tips is rigidly defined and a high pressure leak proof barrier is obtained by means of the holes 39A, 39B and seals 44A, 44B.

It is possible to adjust the optical path length from a few tens of microns to several centimeters such as to adapt the spectroscopy to the type of fluid to be analyzed (from light to dark crude oils, gas condensates, dry gas, etc). This represents a drastic improvement over known optical measurement devices using windows. The adjustment of the position of the probes, i.e. optical path 56 length can be made small or large. This adjustment is made at the manufacturing of the downhole optical chemical compound monitoring device 30. Alternatively, the optical path 56 length can be changed at a later time by an operator, either during the maintenance of the bottom hole assembly, or when the bottom hole assembly is at the surface. The optical path length 56 may be selected according to attenuation factors to be measured. The attenuation factor may range from several orders of magnitude which require an optical path length from a few tens of microns to a few millimeters depending on fluid composition and light wavelengths. The invention enables a fine definition of the optical path length 56 by sliding the optical probe into the holes 39A, 39B as hereinbefore described.

FIGS. 12 to 18 schematically illustrate a downhole optical chemical compound monitoring device 30 according to a second embodiment of the invention. According to the second embodiment, the open cavity 140 of the optical analysis cell part 31 extends perpendicularly to the longitudinal axis YY'. The open cavity 140 has the shape of a trench crossing from side to side. It may further comprise a top opening having inclined edges forming a funnel like shape. This particular configuration of the optical analysis cell part 31 enables reducing the length of the optical probes 141A and 141B. Thus, it is possible to reduce or even eliminate the need for optical fibers. The protective tubes 47A, 47B of the first embodiment take here the shape of protective housings 147A, 147B that further support the electronic circuit boards 57, 58, and the light source 157 and light detector 158, respectively. In addition having such a transverse open cavity 140 is well adapted to drilling fluid (mud) flow when rotation of the mandrel of the bottom hole assembly occurs (drill string rotation during drilling operation).

Figure 12:
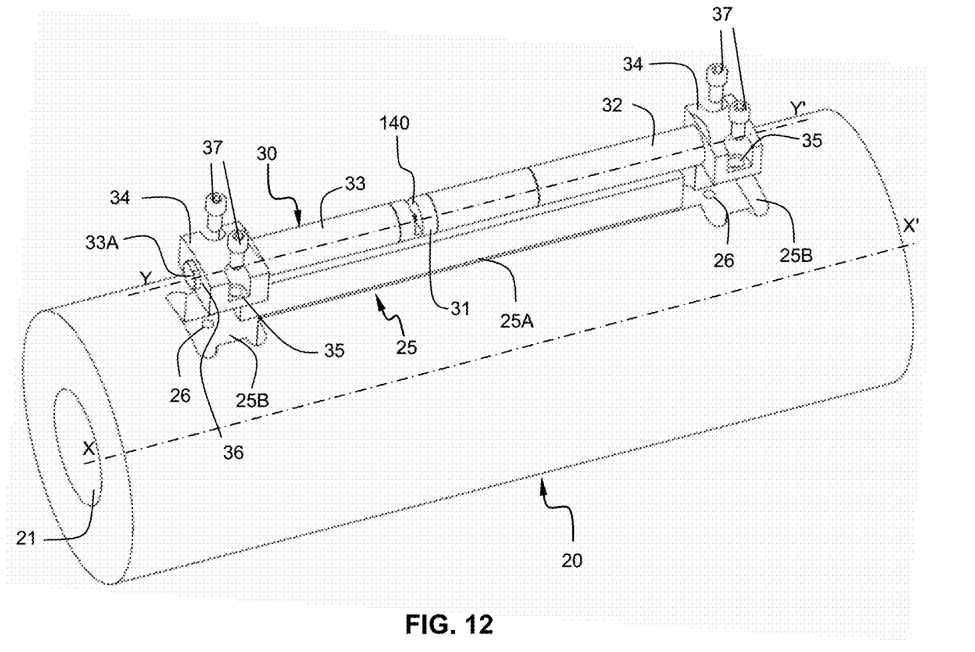
FIG. 12 is perspective partially exploded view showing a connection of a downhole optical chemical compound monitoring device according to a second embodiment of the invention to a mandrel of a bottom hole assembly.
Figure 13:
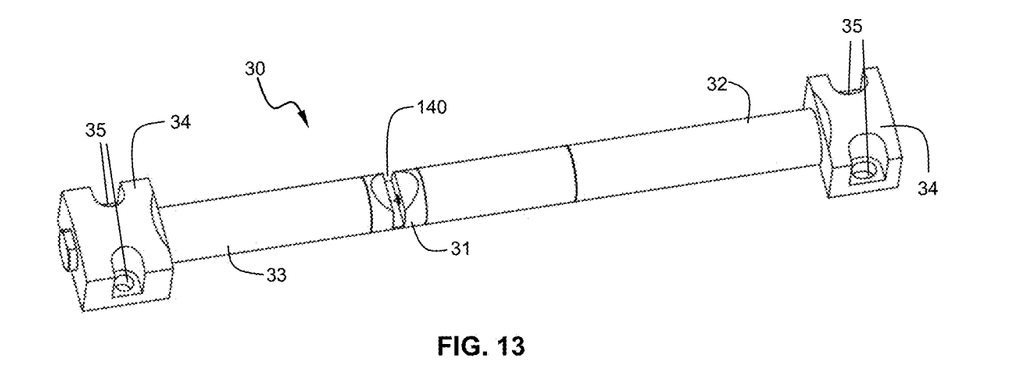
FIGS. 13, 14, 15 and 16 are a top perspective view, a side view, a top view and a longitudinal cross section view of the embodiment of FIG. 12, respectively.
Figure 14:
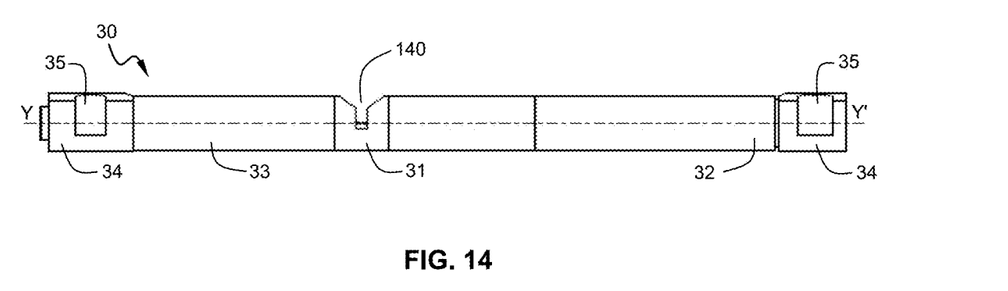
Figure 15:
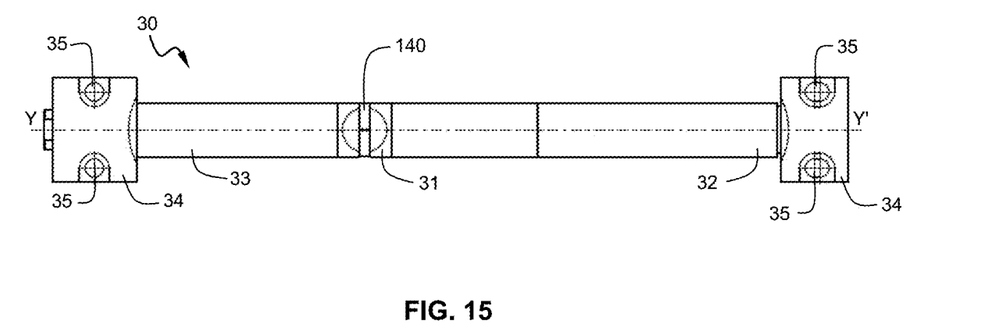

FIG. 12 is perspective partially exploded view showing a connection of a downhole optical chemical compound monitoring device 30 according to the second embodiment of the invention to the mandrel 20. The connection is similar to the first embodiment. FIGS. 13, 14 and 15 are a top perspective view, a side view and a top view of the embodiment of FIG. 12, respectively. The open cavity 140 of the optical analysis cell part 31 extends perpendicularly to the longitudinal axis YY'.

Figure 16:
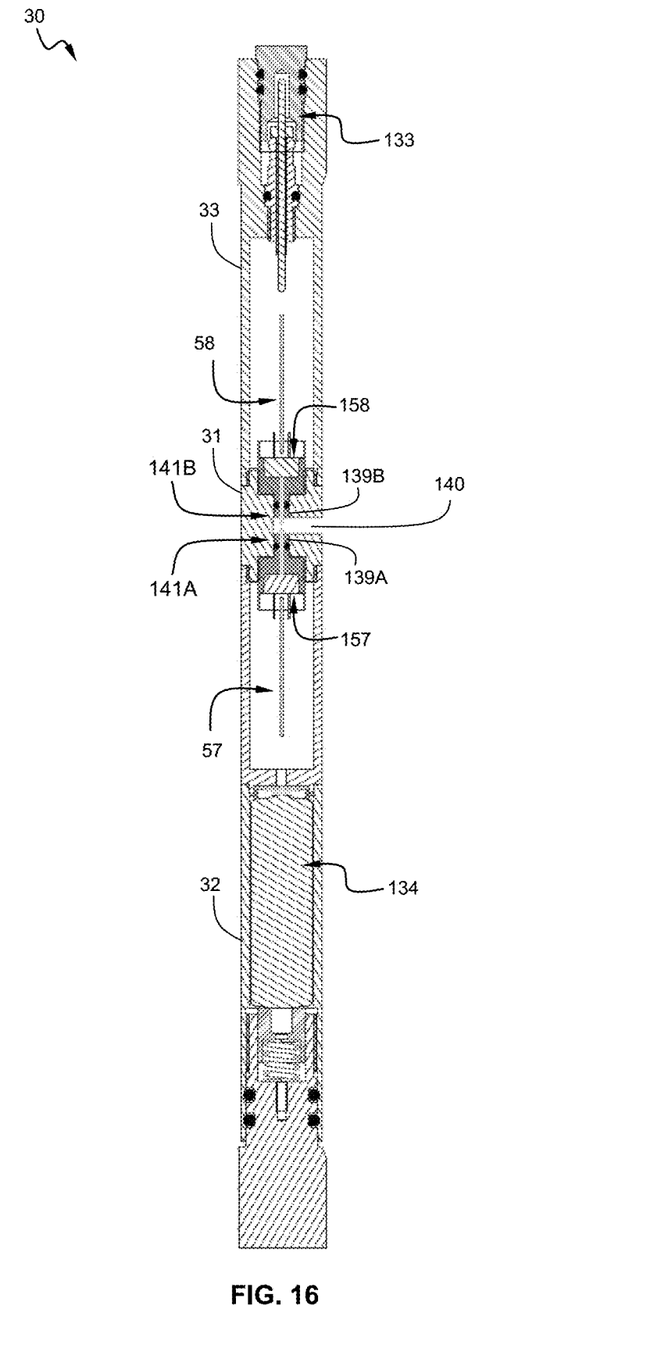
Figure 17:
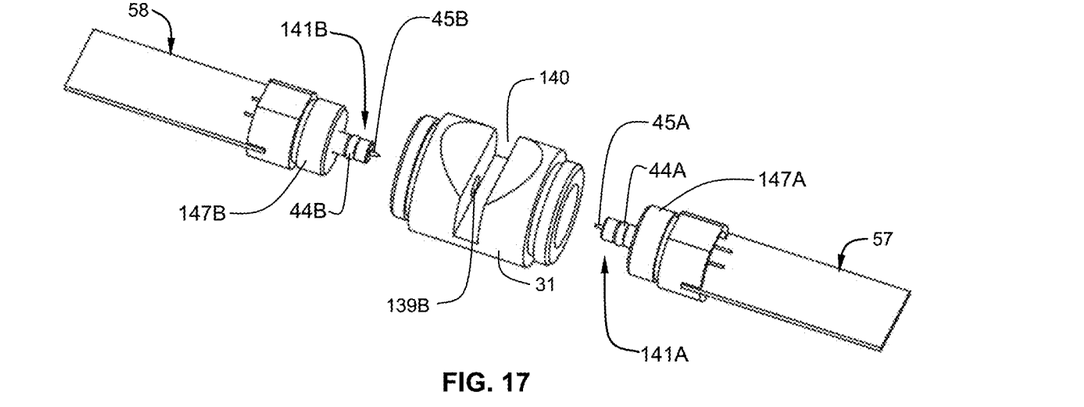
FIGS. 17 and 18 are a perspective partially exploded view and a longitudinal cross section view showing details of the embodiment of FIG. 12, respectively.
Figure 18:
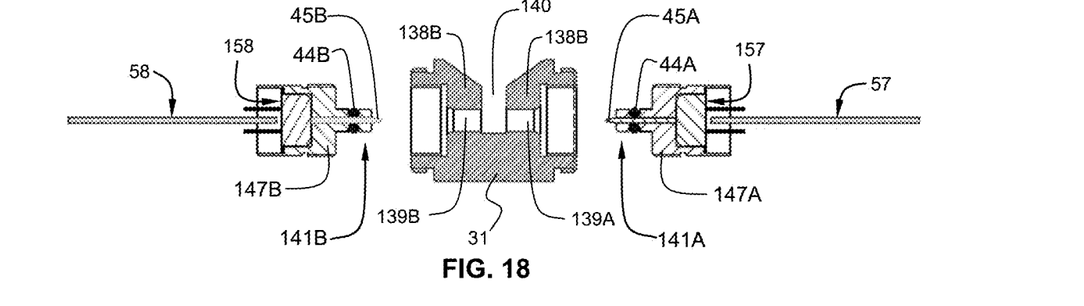

FIG. 16 is a longitudinal cross section view of the second embodiment. FIGS. 17 and 18 are a perspective partially exploded view and a longitudinal cross section view showing details of the optical analysis cell part 31 and connection with the first and second optical probes 141A and 141B with associated electronic circuit board 57 and 58 of the embodiment of FIG. 12, respectively.

The first probe 141A comprises a protective housing 147A that supports and receives, on one side, the electronic circuit boards 57 and the light source 157, and, on the other side, the optical tip 45A. On an external part of the optical tip side, a circumferential groove receives an O-ring seal 44A. The second probe 141B comprises a protective housing 147B that supports and receives, on one side, the electronic circuit boards 58 and the light detector 158, and, on the other side, the optical tip 45B. On an external part of the electronic components side, a circumference is threaded. On an external part of the optical tip side, a circumferential groove receives an O-ring seal 44B. In this embodiment, the optical tip 45A, respectively 45B is directly coupled to the light source 157, respectively the light detector 158. A very compact assembly can be achieved in this way.

The optical analysis cell part 31 comprises two facing holes 39A and 39B oriented along the longitudinal axis YY' and emerging from the facing walls 138A, 138B into the open cavity 140. Said holes 139A and 139B are arranged to receive the two facing optical probes 141A and 141B, respectively. More precisely, the hole 139A (respectively 139B) has an internal shoulder and is internally tapped to form a threaded connection with the protective housing 147A (respectively 147B) of the optical probe 141A (respectively 141B). In this way, it possible to achieve an efficient sealing and to precisely define the distance between the optical probes tips.

The second embodiment depicted in FIG. 16 further illustrates a power unit 134 (e.g. a battery and appropriate power circuitry) positioned within the first part 32, and a telemetry or storing unit 133 positioned within the second part 33.

Figure 19:
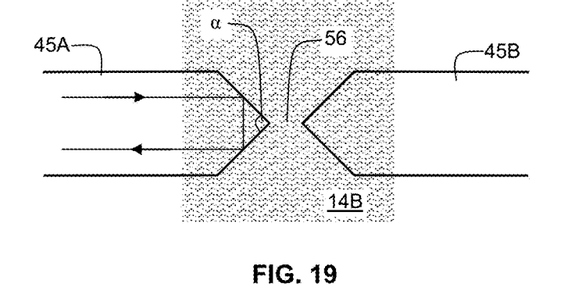
FIGS. 19 and 20 illustrate an alternative optical tip in different type of fluid.
Figure 20:
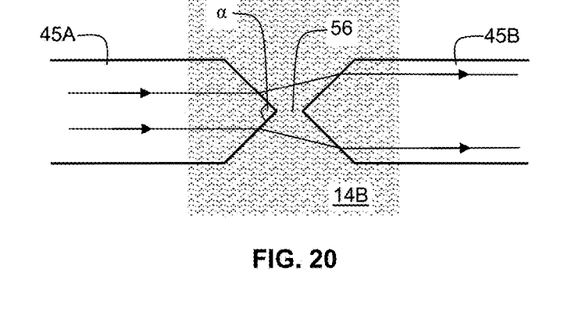

FIGS. 19 and 20 illustrate an embodiment of the optical probe wherein the sapphire tip 45A, 45B has a conical shape with a tip angle α of 90°. In the presence of gas (FIG. 19), there is a total reflection at the light emitting probe tip 45A, there is no light received at the light receiving probe tip 45B. In the presence of oil (FIG. 20), light is transmitted from the light emitting probe tip 45A towards the light receiving probe tip 45B (i.e. Transmission measurements). Therefore, such a tip enables discriminating gas from liquid. Further, the sharp end of the sapphire tip 45A, 45B promotes fluid droplets removal from the optical path 56.

Figure 21:
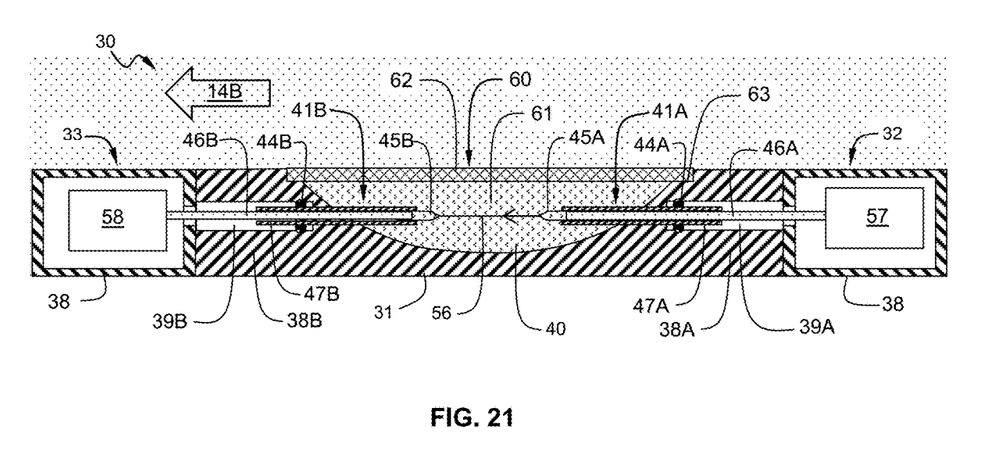
FIG. 21 is side cross section view in the embodiment of FIG. 2 further comprising an anti-contamination filter.

FIG. 21 is side cross section view in a downhole optical chemical compound monitoring device 30 according to the above-mentioned embodiment further comprising an anti-contamination filter 60. The anti-contamination filter 60 in the simpler embodiment includes a buffer fluid 61 that fills in the open cavity 40. The buffer fluid may be a liquid or gel, for example including perfluoropolyether oil (e.g. the product "Fomblin" commercialized by the company Sigma-Aldrich). The function of the buffer fluid is to enable gas present in the drilling fluid 14B diffusing through the buffer fluid, while avoiding, at least significantly reducing drilling mud (liquid and particles) to contaminate the optical tips 45A and 45B, and the optical path length 56. In this particular embodiment, the important aspect is to detect gas in an accurate manner, for example to detect methane gas kick at an early stage. The anti-contamination filter 60 in an enhanced embodiment may further include a grid 62 above the cavity 40 in order to efficiently maintain the buffer fluid 61 in the open cavity 40. The grid 62 may be secure in a clearance 63 around the top portion of the cavity 40 flush with the external surface of the optical analysis cell part 31. The grid 62 may be covered with a non-stick coating, for example by polytetrafluoroethylene (e.g. Teflon commercialized by company Chemours formerly company DuPont). The non-stick coating enables limiting grid fouling. The anti-contamination filter 60 may also be used with the other embodiments, in particular to protect against contamination the open cavity 140 of the embodiments illustrated in FIGS. 12-18.

The fluid optical properties analysis tool of the invention has the following advantages:

The optical path lengths can be made very small thus enabling measurements even in a highly attenuative drilling fluid;

There is no flow restriction, thus enabling measurements even in highly viscous fluids;

There is no dead volume incumbent to the analysis cell assembly, thus cancelling at least greatly reducing analysis cell contamination;

The self cleaning in multiphasic environments is fast, eliminating or at least greatly reducing optical probes contamination;

The optical path lengths is adjustable; and

The integration of downhole optical chemical compound monitoring device in the mandrel of bottom hole assembly is easy.

The drawings and their description hereinbefore illustrate rather than limit the invention.

It should be appreciated that embodiments of the present invention are not limited to embodiments showing a vertical well bore and horizontal well bore, said embodiments may also apply to a deviated/inclined well bore.

It should be appreciated that embodiments of the present invention are not limited to offshore hydrocarbon wells and can also be used onshore hydrocarbon wells.

It should be appreciated by those skilled in the art that any block diagrams herein represent conceptual views of illustrative elements embodying the principles of the invention. Further, the appended drawings are not intended to be drawn to scale.

Any reference sign in a claim should not be construed as limiting the claim. The word "comprising" does not exclude the presence of other elements than those listed in a claim. The word "a" or "an" preceding an element does not exclude the presence of a plurality of such element.

The invention claimed is:

1. A downhole optical chemical compound monitoring device arranged to be integrated in a mandrel of a drilling system, for monitoring a chemical compound in a drilling fluid circulated through a well, the downhole optical chemical compound monitoring device comprising:

an analysis cell part comprising an open cavity into which the drilling fluid is free to flow;

a first optical probe coupled to a light source and arranged to transmit a light energy into the open cavity; and a second optical probe coupled to a detector and arranged to produce in use a signal resulting from an interaction of the drilling fluid present in the open cavity with said light energy, indicative of a quantity of chemical compound present in the drilling fluid;

wherein:

each of said optical probes is mounted through a wall of the analysis cell part in a sealed manner and has a tip, the tip being needle shaped and having an external diameter less than 1 mm; and the first optical probe and the second optical probe are arranged such that the first and second tips of the respective optical probes project into the open cavity and such that the first tip of the first optical probe faces the second tip of the second optical probe at a defined distance ranging from 10 μm to 10 mm.

2. The downhole optical chemical compound monitoring device of claim 1, wherein the analysis cell part comprises a first and a second hole facing each other, a portion of the first and second optical probe being inserted into the open cavity through the first and second hole respectively, and wherein at least one optical probe is coupled in sealed manner to one of the holes, said seal and hole being adapted to enable the position of said optical probe relatively to the wall of the analysis cell part to be adjusted so as to control the defined distance between both tips.

3. The downhole optical chemical compound monitoring device of claim 1, wherein the optical probes are parallel to a longitudinal axis YY' of the analysis cell part.

4. The downhole optical chemical compound monitoring device of claim 1, wherein each optical probe comprises an optical element in the form of an optical fiber and a tip of sapphire or equivalent material located in a central portion of an elongated body in the form of a protective tube, an end portion of said optical element forming a tip end adapted to be in contact in use with the drilling fluid present in the open cavity.

5. The downhole optical chemical compound monitoring device of claim 4, wherein each optical probe further comprises an electronic board coupled to the optical element and integrating a measurement circuit and a processing module so as to deliver digital measurements on an output cable.

6. The downhole optical chemical compound monitoring device of claim 1, wherein each optical probe comprises an optical element in the form of a tip of sapphire or equivalent material located in the central portion of a supporting body forming a protective housing, an end portion of said optical element forming a tip end adapted to be in contact in use with the drilling fluid present in the open cavity.

7. The downhole optical chemical compound monitoring device of claim 6, wherein each optical probe further comprises an electronic board coupled to the optical element and integrating a measurement circuit and a processing module so as to deliver digital measurements on an output cable.

8. The downhole optical chemical compound monitoring device of claim 1, wherein the open cavity has a trench shape comprising an elongated part oriented substantially parallel to the longitudinal axis YY'.

9. The downhole optical chemical compound monitoring device of claim 1, wherein the open cavity has a trench shape comprising an elongated part oriented substantially perpendicular to the longitudinal axis YY'.

10. The downhole optical chemical compound monitoring device of claim 1, further comprising a first part and a second part respectively extending longitudinally according to the longitudinal axis YY' on each side of the analysis cell part, each part forming a protective housing, the first part comprising an optical emission electronic circuit including the light source and the second part comprising an optical reception electronic circuit including the detector.

11. The downhole optical chemical compound monitoring device of claim 1, further comprising at least one supporting part arranged to secure in a removable manner the first part and/or the second part into a corresponding recess of the mandrel of the drilling system.

12. The downhole optical chemical compound monitoring device of claim 1, wherein the light source, respectively the detector, transmits, respectively detects, light energy selected from ultraviolet light, visible light, or near infra-red light.

13. The downhole optical chemical compound monitoring device of claim 1, wherein the detector is tuned to detect characteristic light energy of methane, carbon dioxide or hydrogen sulfide.

14. The downhole optical chemical compound monitoring device of claim 1, wherein the open cavity has internal dimensions ranging between 2 to 15 mm.

15. The downhole optical chemical compound monitoring device of claim 1, further comprising an anti-contamination filter including a buffer fluid filling the open cavity.

16. The downhole optical chemical compound monitoring device of claim 15, wherein the buffer fluid includes perfluoropolyether oil.

17. The downhole optical chemical compound monitoring device of claim 15, wherein the anti-contamination filter further includes a grid above the open cavity.

18. A bottom hole assembly of a drilling system comprising a mandrel having a recess positioned on a mandrel circumference, the recess being arranged to receive a downhole optical chemical compound monitoring device comprising:
an analysis cell part comprising an open cavity into which a drilling fluid is free to flow;
a first optical probe coupled to a light source and arranged to transmit a light energy into the open cavity; and
a second optical probe coupled to a detector and arranged to produce in use a signal resulting from an interaction of the drilling fluid present in the open cavity with said light energy, indicative of a quantity of chemical compound present in the drilling fluid;
wherein:
each of said optical probes is mounted through a wall of the analysis cell part in a sealed manner and has a tip, the tip being needle shaped and having an external diameter less than 1 mm; and
the first optical probe and the second optical probe are arranged such that the first and second tips of the respective optical probes project into the open cavity and such that the first tip of the first optical probe faces the second tip of the second optical probe at a defined distance ranging from 10 µm to 10 mm.

19. A measurements/logging-while-drilling tool of a drilling system comprising a recess positioned on an external surface, the recess being arranged to integrate a downhole optical chemical compound monitoring device comprising:
an analysis cell part comprising an open cavity into which a drilling fluid is free to flow;
a first optical probe coupled to a light source and arranged to transmit a light energy into the open cavity; and
a second optical probe coupled to a detector and arranged to produce in use a signal resulting from an interaction of the drilling fluid present in the open cavity with said light energy, indicative of a quantity of chemical compound present in the drilling fluid;
wherein:
each of said optical probes is mounted through a wall of the analysis cell part in a sealed manner and has a tip, the tip being needle shaped and having an external diameter less than 1 mm; and
the first optical probe and the second optical probe are arranged such that the first and second tips of the respective optical probes project into the open cavity and such that the first tip of the first optical probe faces the second tip of the second optical probe at a defined distance ranging from 10 µm to 10 mm.

* * * * *